United States Patent [19]

Kohsaka et al.

[11] 4,449,816
[45] May 22, 1984

[54] METHOD FOR MEASURING THE NUMBER OF HYPERFINE PARTICLES AND A MEASURING SYSTEM THEREFOR

[75] Inventors: Yasuo Kohsaka, Sakai; Yoshihiro Nonaka; Hideo Tachibana, both of Fujiidera, all of Japan

[73] Assignee: Nitta Gelatin Kabushiki Kaisha, Osaka, Japan

[21] Appl. No.: 262,550

[22] Filed: May 11, 1981

[51] Int. Cl.³ .................. G01N 1/00; G01N 15/02
[52] U.S. Cl. .................................... 356/37; 73/28; 356/336; 356/338
[58] Field of Search ............ 356/37, 336, 338, 339; 73/28; 340/627

[56] References Cited

U.S. PATENT DOCUMENTS

| | | | |
|---|---|---|---|
| 3,007,367 | 11/1961 | Rich | 356/37 |
| 3,351,759 | 11/1967 | Rich | 73/28 |
| 3,458,284 | 7/1969 | Rich et al. | 356/37 |
| 3,592,546 | 7/1971 | Gussman | 356/37 |
| 3,694,085 | 9/1972 | Rich | 356/37 |
| 4,293,217 | 10/1981 | Bird, Jr. et al. | 356/37 |

Primary Examiner—Vincent P. McGraw
Attorney, Agent, or Firm—Maky, Renner, Otto & Boisselle

[57] ABSTRACT

A method and a system for measuring the number of hyperfine particles comprising the step in which an air aerosol containing fine particles is led into a saturated vapor chamber and a high temperature saturated vapor chamber, respectively, to produce saturated vapor aerosols, the step in which the two saturated vapor aerosols produced as aforenoted are led into a mixing chamber, so that the aforementioned vapor is condensed on the aerosol particles as the nuclei, thereby achieving growth of the aforementioned fine particles, and the step for measuring the number of the said fine particles grown in that way.

13 Cla

METHOD FOR MEASURING THE NUMBER OF HYPERFINE PARTICLES AND A MEASURING SYSTEM THEREFOR

DETAILED DESCRIPTION OF THE INVENTION

Figure 1:
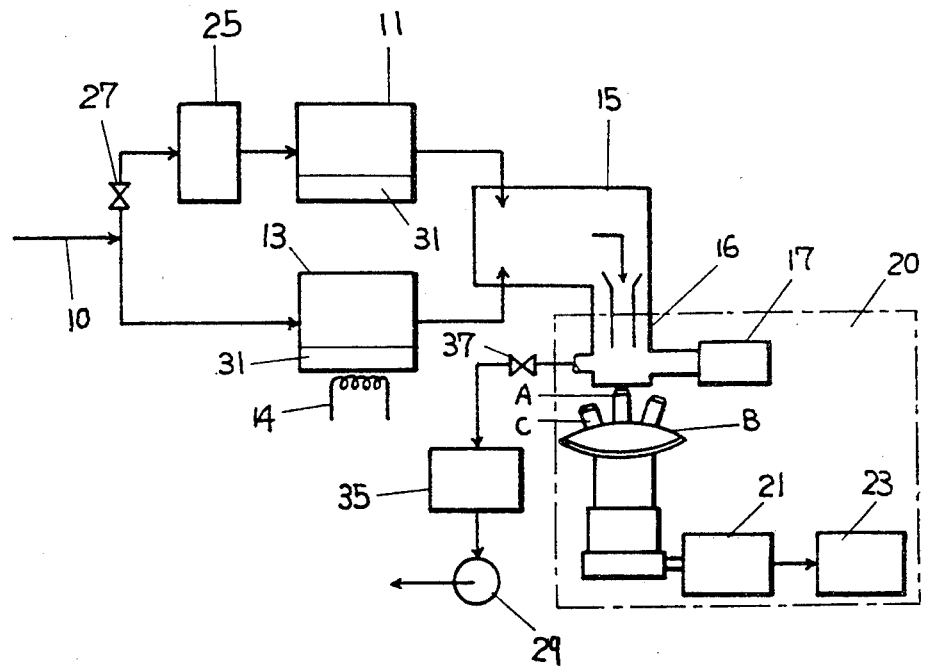

The present invention relates to a novel measuring method and measuring system therefor for measuring the number of hyperfine particles floating in air.

Of late, in the technical fields covering air cleaning for manufacture of integrated circuits, sterilized chambers, radiations, exhaust gases and atmospheric pollution, etc., measurement of particle diameter, the number, etc. of hyperfine particles in air has emerged as an important theme. Thus in dealing with such items by way of control or regulation, there arises the need for the measurement of the particle diameter and the number of hyperfine particles, and significant improvement in this technique is desired. Against this background, the present invention is intended to provide a novel method and system for measuring the number of hyperfine particles by making use of a condensation nuclei counter. Further, this invention pertains to a novel method and system for measuring the number of hyperfine particles or methods and systems for measuring the particle diameter distribution of hyperfine particles in which other instruments including, for examples, diffusion tubes, diffusion battery, differential mobility analyzer and electrical aerosol analyzer are used in conjunction with this system, to take the measurements of the numbers of particles in respective grades differing in their particle diameters into which grades widely spead particle sizes are stepwise divided.

The condensation nuclei counter is designed to detect the number of hyperfine particles having particle diameters smaller than 1 $\mu$m in a gas (particularly, air). Since particles being smaller than 0.1 $\mu$m are equivalent to, or smaller than, the mean free path of gas or the wave lengths of visible light rays, they cannot be optically detected in the state of being floated in gas as they are. In the condensation nuclei counter, some appropriate vapor (commonly employed is steam or alcohol vapor) is condensed on the aerosol particles as the nuclei; the aggregates are grown, and made coarser to be optically observable, and then, their number is counted.

In many types of conventional condensation nuclei counters, air containing fine particles is saturated with steam; this air is subjected to adiabatic expansion by means of a piston or timing valve and vacuum pump, etc. to form a supersaturated atomosphere; then the steam with which the air is supersaturated is condensed on the particles to be coarser aggregates, the number of which is counted by observation under a microscope. These types are operatable merely in batch or in intermittent fashion. This invention provides a condensation nuclei counter which has been freed from such limitations.

In condensation nuclei counters which have become available relatively recently, the aerosol saturated with alcohol vapor is quenched by means of a cooling nozzle which works by taking advantage of the Peltier effect. According to this method, higher degrees of supersaturation can not be achieved, and the sizes of the particles which are to form the nuclei are limited. Since no vapor could condense on particles having dimensions smaller than a certain value, particles smaller than that size are not countable. Moreover, because wall surface of the cooling nozzle is being cooled, thermophoresis takes place, while the aerosol is passing through the nozzle, causing the aerosol particles to deposit on the wall surface of the nozzle. This invention provides a novel condensation nuclei counter in which such drawbacks have been eliminated.

Figure 2:
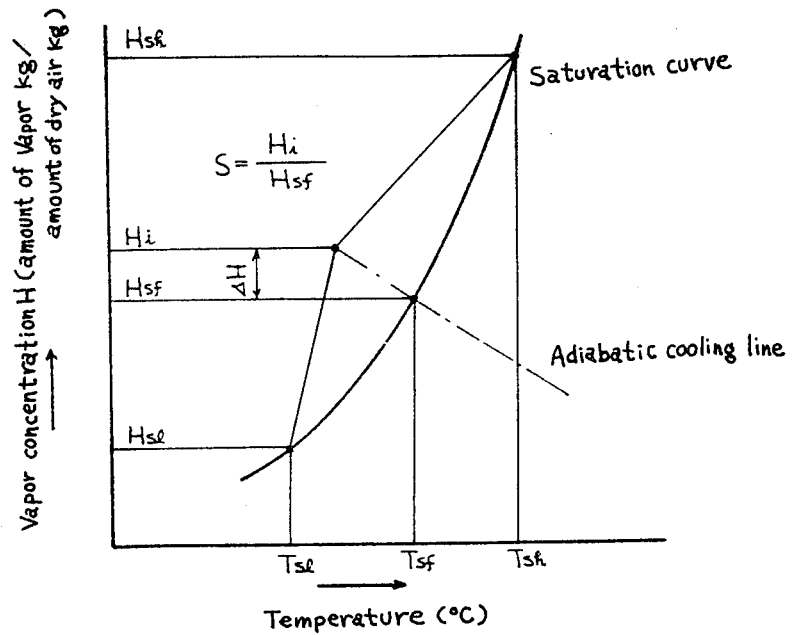
Figure 3:
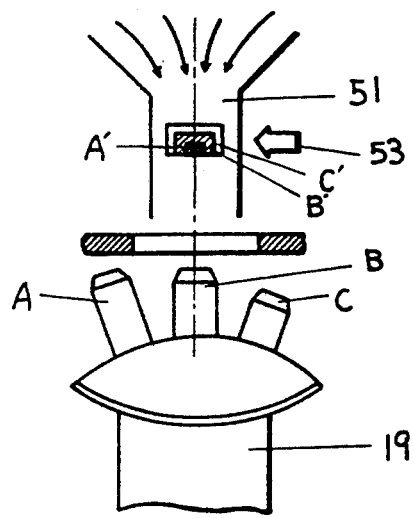
Figure 4:
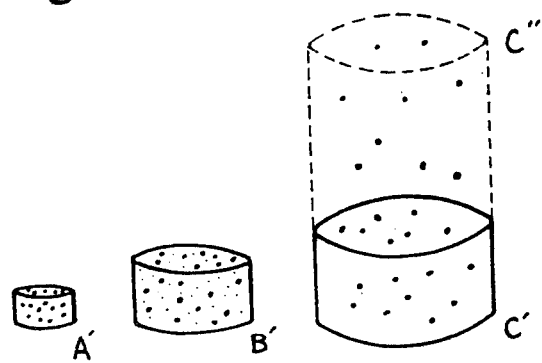
Figure 5:
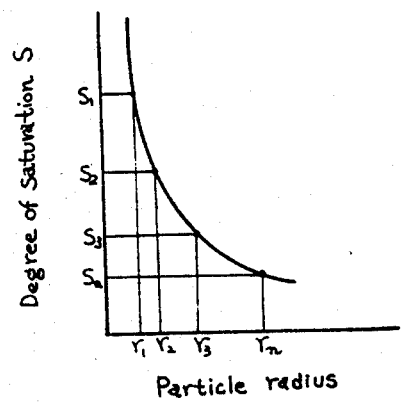

In the following, the method for measuring the number of hyperfine particles and the measuring system therefor according to this invention are described with reference to the annexed drawings of which:

FIG. 1 depicts a constructional block diagram of the system of this invention for explanation of the measuring method;

FIG. 2 gives a temperature-vapor concentration graph for explanation of condensation rate;

FIGS. 3 and 4 present a sketch and a chart for explanation of the roles played by the plurality of objectives with which the microscope is provided;

FIG. 5 provides a graph to show how the smallest countable particle diameter is altered by the variation of the limit values of S.

Figure 6:
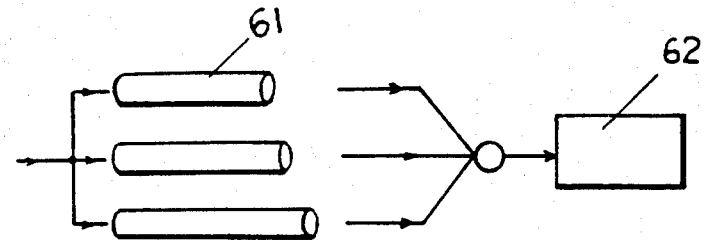
Figure 7:
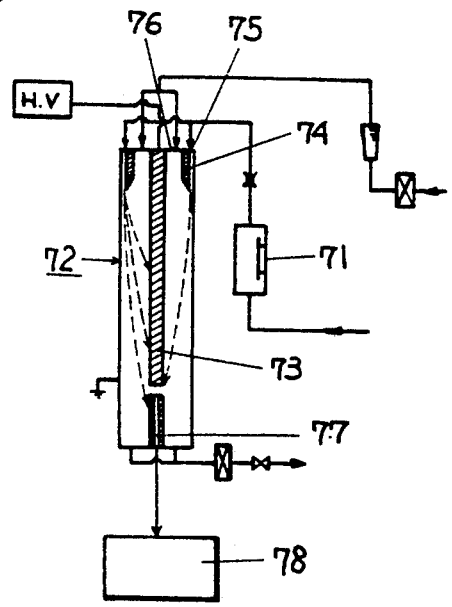
Figure 8:
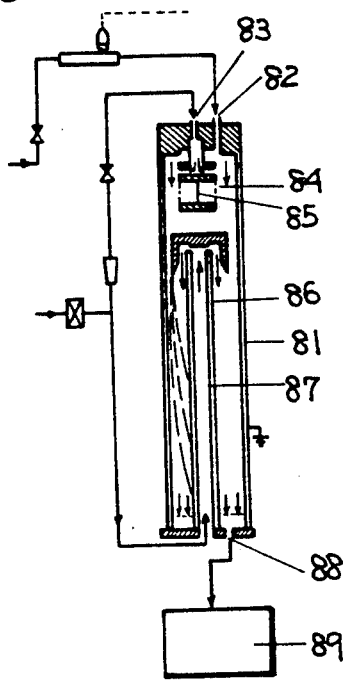
Figure 9A:
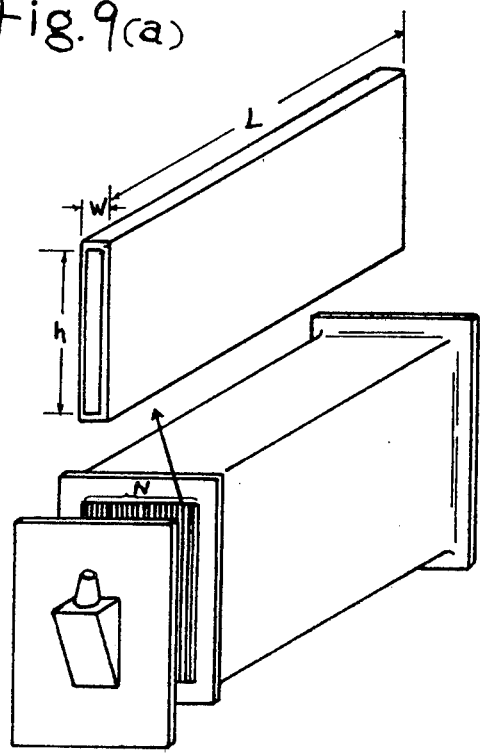
Figure 9B:
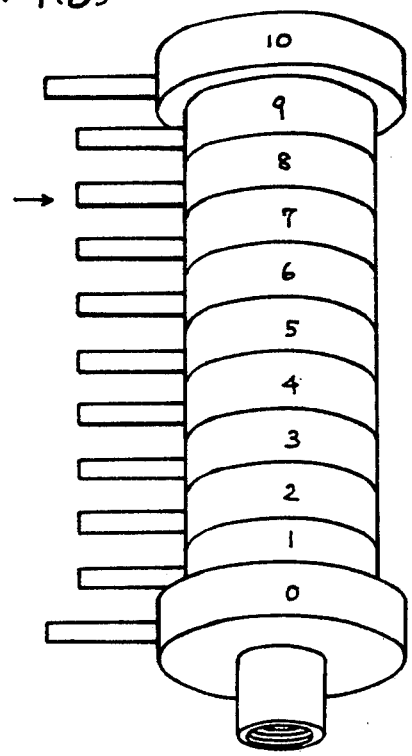
Figure 9C:
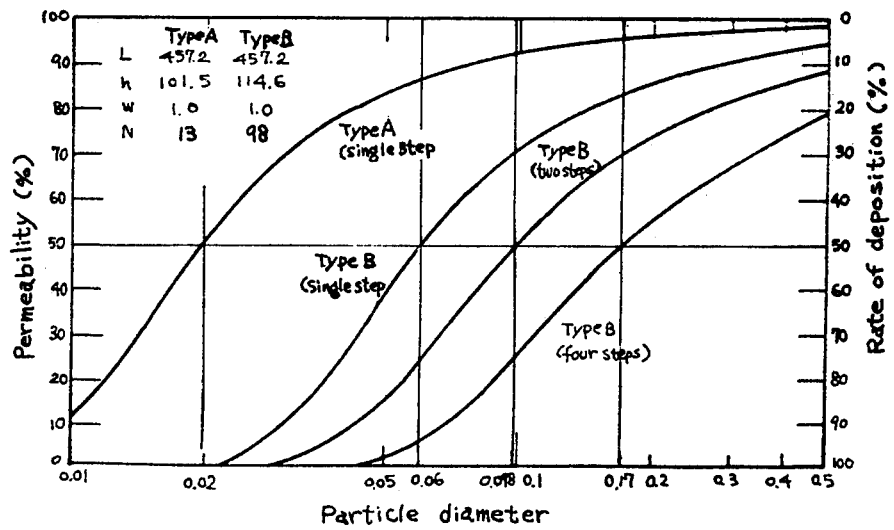

FIG. 6 denotes a simulated diagram of an embodiment of this invention having diffusion tubes;

FIG. 7 designates a diagram showing the construction of an embodiment of this invention making use of a differential mobility analyzer;

FIG. 8 identifies a diagram showing the construction of another embodiment of this invention using an electrical aerosol analyzer in conjunction therewith;

FIGS. 9, (a) and (b), exhibit perspective views of diffusion batteries to be used in association with the system of this invention, and FIG. 9 (c) draws up curves representing the theoretical permeability when the flow rate of aerosol in the diffusion battery is 6 l/min.

For convenience the following important reference numerals and the parts to which they refer are listed below:

10 ... Aerosol inlet; 11 ... Saturated vapor chamber; 13 ... High temperature saturated vapor chamber; 14 ... Heating means; 15 ... Mixing chamber; 16 ... Delivery section; 17 ... He-Ne Laser light source, 19 ... Microscope; 21 ... TV Camera; 23 ... Picture image analyzing device; 25, 35 ... Flow-meters, 27, 37 ... Valves; 29 ... Vacuum pump, 31 ... Solvent; 51 ... Observation cell; 53 ... Laser beam.

FIG. 1 shows a block diagram for explanation of the method and the system according to this invention. The aerosol coming from aerosol inlet (10) is led to saturated vapor chamber (11) through a valve (27) and a flowmeter (25). Along another route, the aerosol is led to high temperature vapor chamber (13). The high temperature vapor chamber (13) is held at a higher temperature than that of the saturated vapor chamber (11) by a heating means (14), and both saturated vapor chambers are fully filled with saturated vapor of a solvent (31). For the solvent, water, ethanol, etc. may be utilized. As these vapor aerosols are mixed adiabatically in mixing chamber (15), the vapor condenses and makes growth on the aerosol particles as the nuclei into such a size large enough to cause scattering of light as hereinafter described. In this process, the flow rates and the temperature difference in the saturated vapor chamber (11) and the high temperature vapor chamber (13) are essential elements, which may be determined by the balances of calorific heat and materials of the whole. It is for this reason necessary that the correct flow rate should be monitored by the flowmeter (25), and in response thereto, the flow rate should be exactly controlled by means of the valve (27). FIG. 2 gives a schematic representation of these relationships for explanation superposed on the temperature-vapor concentration graph, ΔH marked in the graph indicating the condensed amount of the vapor. This amount determines to what extent the particles can be grown. It may be determined also by reference to the balances of calorific heat and materials. Since the vapor pressure on the particle surfaces rises due to the Kelvin effect, as the aerosol particles become critically smaller, as previously stated, in order to bring about condensation on the particles as the nuclei, a vapor pressure greater than the amount of the pressure rise must be applied on the particles. In this connection, $S = H_i/H_{sf}$ marked in FIG. 2 is a designated degree of supersaturation. This S must be adequately large, if small particles are to be grown. If this value is too large, condensation will occur even in the absence of particles which are to serve as the nuclei, giving rise to the so called homogeneous nucleation. The limit degrees of supersaturation should be 4.85 for steam, while ethanol vapor's is limited to 2.35. Accordingly, it is most desirable to operate the condensation nuclei counter at these limit values. According to the method of this invention, by making the control for the degree of supersaturation, thru adjustment of the flow-rate by way of operation of valve (27), while adjusting the temperature change by a heating means (14), the nuclear condensation is intended to take place in the optimal conditions. Thus according to the method of this invention, however small, the particles may be grown, and made coarser continuously and with high stability.

The condensed and grown particles are led to measuring mechanism (20) by the force of a vacuum pump (29). Thus they pass through delivery section (16), then, through a valve (37) and a flowmeter (35), and are discharged through the vacuum pump (29). The methods for optically counting the particles grown in this way include the light scattering method and the method by use of an ultramicroscope, the latter commanding a wider countable concentration range than the former. On this ground, the method by use of an ultramicroscope as shown in FIG. 1 is hereby adopted. To the grown particles entering the delivery section (16), a light beam is projected in the transverse direction from a He-Ne laser light source (17), so that the light rays scattered by the particles are observed under a microscope (19) so arranged that it has its optical axis in the same direction as that of the flow of the particles. To this microscope (19), a TV camera (21) is attached to automatically project the picture image thereon, and an arrangement is further made, so that the number of particles may be automatically and continuously counted by means of picture image analyzing apparatus (23). This microscope (19) is equipped with objectives having different focal distances, for example, A, B and C, and in correspondence thereto, different visual field spaces indicated by A', B' and C' are formed inside the space in observation cell (51), as shown in FIG. 3. (53) denotes the laser beam. Different lenses A, B and C should be employed according to the concentrations of particles as shown in FIG. 4. As the number of particles seen in the visual field is reduced by using the lense A with a high multiplicity for high concentrations of particles, the counting miss of counting more than two particles as an apparent single particle due to overlapping of light rays scattered by them is preventable. With declining concentrations, the field of vision should be expanded to B' and C' with multiplicity reduced correspondingly. In one case, the countings of particles for the visual field parts of A', B' and C' were made in 1/60 second. The flow rate of aerosol in the observation cell is determined by the focal depth and the counting time. If the concentration is as low as less than 1 particle/cm$^3$, the counts are integrated for several seconds with the aerosol being continuously passed through the cell. The resultant volume of the visual field will be that as represented by C' in FIG. 4. Thus according to this invention, exact measurement of the number of particles can be made over such very wide range of particle concentrations as $10^{-3}$ particles/cm$^3 \sim 10^6$ particles/cm$^3$. Furthermore, this invention enables providing a condensation nuclei counter simple in construction and operation, which permits continuous operation, always at the optimal degrees of condensation, and affords wide counting ranges.

While in the above description, for counting the number of particles, the degree of supersaturation is set to the limits, when the value of S is changed as $S_1, S_2 \ldots S_n$, as shown in FIG. 5, the minimum values of the grown particle diameters are correspondingly determined as $r_1, r_2 \ldots r_n$. Thus the number of particles having dimensions larger than the respective values of r is countable, and accordingly, it is possible to measure the number of particles having diameters falling between $r_1 \sim r_2$ by deducting the number of particles having diameters larger than $r_1$. In that way, this system can play the role of a particle diameter distribution measuring system. According to this invention, the control of such limit values S can be performed quite easily.

In still another application, as shown in FIG. 6, use is made of a specified number of diffusion tubes (61) having different diffusion lengths to take advantage of the change in the diffusion rates with varying particle diameters; then the numbers of particles of aerosol which have passed respective diffusion tubes are counted by means of this system; in that way, this system may be utilized as a particle diameter distribution measuring system just as it is made to serve that end by changing the limit values S as hereabove described. (62) stands for the measuring system of this invention. In place of the diffusion tubes, a diffusion battery provided with a plurality of compartments having different diffusion lengths may be put to use for this purpose.

The diffusion battery is composed of a certain number of diffusion channels (oblong rectangular grooves, a group of tubes with small bores, series-connected screens, etc.). By altering the lengths and the numbers of the diffusion channels and the flow rates of aerosol in these channels, the countable particle diameter ranges of the aerosol the particle numbers of which are to be counted may be changed. The aerosol particles, while in flowing in each diffusion channel, diffuse to, and are deposited on, the wall of the said channel at the rate calculated from the dimensions of said channel and the particle diameters, and only part of them, then, come out through the outlet. This phenomenon is utilized to determine the particle diameter distribution of the aerosol particles.

Such diffusion batteries include, for example, the type of parallel flat plates construction as shown in FIG. 9 (a) and the type of screen construction as shown in FIG. 9 (b).

These ways of application permit this system to be used not only for counting the number of hyperfine particles having diameters down to 0.001 μm, but also for measuring the particle diameter distribution for a range of 0.001~0.5 μm.

Combination of this system with a differential mobility analyzer which selects single dispersed particles from among multiple dispersed particles by taking advantage of the mutual action between the charged particles and an electric field permits it to advance from the measurement of the number of particles to its use as a particle diameter distribution measuring system.

Thus adoption of such compositions as shown in FIGS. 7 and 8 enables this system to advance from its use for measuring the number of particles to its utilization for the measurement of particle diameter distribution.

FIG. 7 portrays a construction having a differential mobility analyzer combined with the measuring system of this invention. Referring to this Figure, the aerosol having been charged at the radiation source (71) is led into the analyzer (72). The analyzer (72) is cylindrical in shape having, at its center, central rod (73) on which a D.C. high voltage is impressed, and having, at the top of the cylinder, inlets (75) and (76) formed by a diaphragm (74).

Then from the inlet (75), aerosol, and from the inlet (76), clean air are respectively led in. Depending on the intensity of the electric field produced by the central rod (73) and the axial air flow-rate, particles smaller than the specified size deposit on the central rod (73), while particles larger than that are led out through a small hole (77) located at the bottom of the cylinder; these particles are, then, brought to the measuring system (78) of this invention.

FIG. 8 shows a construction combining an electrical aerosol analyzer with the system of this invention. Referring to this Figure, the aerosol and sheath air are led into the analyzer. The analyzer (81) cylindrical in shape has, at the top of the cylinder, an inlet (82) for leading in the aerosol and another inlet (83) for leading in sheath air, and has, at the center and therebelow, charging section (84) to which a high voltage is fed. At the charging section (84), corona discharge is effected by a core wire (85), thereby to get the flowing aerosol particles carried by the sheath air charged. Of the charged particles, depending on the axial flow of clean air introduced from the inside of the inner cylinder (86) and the intensity of the electric wave, particles smaller than the predetermined size are deposited on the outer surface (87) of the inner cylinder, but those larger than that are discharged through small hole (88) located at the bottom of the cylinder. These particles are, then, delivered into the system (89) of this invention.

As described just hereabove, by utilizing constructions of FIGS. 7 and 8, the measuring system of this invention has more prominent effects.

What is claimed:

1. A method for measuring the number of hyperfine particles in an aerosol comprising the steps of producing saturated vapor aerosols by dividing an incoming unfiltered aerosol to flow along first and second paths, passing the unfiltered aerosol flowing on said first path through a first vapor chamber saturated with a solvent and at a first temperature, passing the unfiltered aerosol flowing on said second path through a second vapor chamber saturated with the solvent and at a second temperature higher than the first temperature, thereafter delivering the two vapor saturated aerosols to a mixing chamber, so that the vapors are condensed from the resulting supersaturated mixture on the aerosol particles as the nuclei, thereby achieving growth of the aforementioned fine particles, and measuring the number of such fine particles so grown.

2. A method as defined in claim 1, wherein said measuring step comprises measuring the intensity of the light scattered such fine particles.

3. A method as defined in claim 1, wherein said measuring step comprises directing a light beam to such grown fine particles, and observing the light scattered by such grown fine particles to count their number under a microscope associated with TV camera.

4. A method as defined in claim 1, wherein said step of producing comprises adjusting the flow rate of aerosol flowing in at least one of the first and second paths, and heating the solvent in the second vapor chamber.

5. A method as defined in claim 1, wherein said step of producing comprises altering the degree of supersaturation such that in said step for measuring the number of the grown fine particles, the particle diameter distribution may be measured by measuring the number of particles for the respective degrees of supersaturation.

6. A method as defined in claims 1, 2, 3, 4 or 5, said measuring comprising directing such grown particles through at least several types of diffusion tubes having different lengths or a diffusion battery, and simultaneously measuring particle diameters and distribution.

7. A method as defined in claims 1, 2, 3, 4 or 5, said measuring comprising directing such grown particles through a differential mobility analyzer or an electrical aerosol analyzer, and simultaneously measuring particle diameters and particle diameter distribution.

8. A system for measuring the number of hyperfine particles in an aerosol comprising a saturated vapor chamber and a high temperature saturated vapor chamber into which an air aerosol containing fine particles may be delivered to produce two saturated vapor aerosols, a mixing chamber means for mixing the two saturated vapor aerosols produced, and a measuring means for counting the number of aerosol particles grown with the vapor condensed thereon in the said mixing chamber means.

9. A measuring system as defined in claim 8, further comprising means for regulating of the degree of supersaturation in the aforementioned mixing chamber means, including flow lines for delivering such aerosols to said saturated vapor chambers, adjusting means for adjusting the flow rate of the aerosol in at least one of said flow lines, and heating means in said high temperature saturated vapor chamber for heating the same.

10. A measuring system as defined in claim 8, wherein said measuring means comprises a delivery section located in a part of said mixing chamber means, a microscope means for observing the aerosol particles in the said delivery section, and a light source means for irradiating said delivery section in a transverse direction.

11. A measuring system as defined in claim 10, wherein said microscope means has a plurality of objectives having different focal distances.

12. A measuring system as defined in claims 8, 9, 10 or 11, said measuring means comprising several types of diffusion tubes having different lengths or a diffusion battery, and means simultaneously measuring particle diameters and distribution.

13. A system as defined in claims 8, 9, 10 or 11 said measuring means comprising a differential mobility analyzer or an electrical aerosol analyzer, and means for simultaneously measuring particle diameters and particle diameter distribution.

* * * * *